United States Patent [19]
Lee et al.

[11] Patent Number: 5,911,737
[45] Date of Patent: Jun. 15, 1999

[54] MICROFABRICATED THERAPEUTIC ACTUATORS

[75] Inventors: Abraham P. Lee, Walnut Creek; M. Allen Northrup, Berkeley; Dino R. Ciarlo, Livermore; Peter A. Krulevitch, Pleasanton; William J. Benett, Livermore, all of Calif.

[73] Assignee: The Regents of the University of California, Oakland, Calif.

[21] Appl. No.: 08/807,412

[22] Filed: Feb. 28, 1997

[51] Int. Cl.⁶ .................................................. A61B 17/28
[52] U.S. Cl. ............................... 606/209; 128/898; 606/1
[58] Field of Search ............................... 128/898; 606/1, 606/205, 206, 207, 211

[56] References Cited

U.S. PATENT DOCUMENTS 5,609,608  3/1997  Benett et al. ............................ 606/205
5,658,515  8/1997  Lee et al. ................................ 264/219

*Primary Examiner*—Michael Buiz
*Assistant Examiner*—Kevin Truong
*Attorney, Agent, or Firm*—L. E. Carnahan

[57] ABSTRACT

Microfabricated therapeutic actuators are fabricated using a shape memory polymer (SMP), a polyurethane-based material that undergoes a phase transformation at a specified temperature (Tg). At a temperature above temperature Tg material is soft and can be easily reshaped into another configuration. As the temperature is lowered below temperature Tg the new shape is fixed and locked in as long as the material stays below temperature Tg. Upon reheating the material to a temperature above Tg, the material will return to its original shape. By the use of such SMP material, SMP microtubing can be used as a release actuator for the delivery of embolic coils through catheters into aneurysms, for example. The microtubing can be manufactured in various sizes and the phase change temperature Tg is determinate for an intended temperature target and intended use.

9 Claims, 2 Drawing Sheets

MICROFABRICATED THERAPEUTIC ACTUATORS

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to microfabricated actuators, particularly to microactuators for use in catheter-based interventional therapies or remote micro-assembly applications, and more particularly to microfabricated therapeutic actuators utilizing shape memory polymer microtubing as a release actuator mechanism.

Microactuators for remote and precise manipulation of small objects is of great interest in a wide variety of applications. Recently, substantial efforts have been directed to the development of microactuators or microgrippers for various application, and which are particularly useful in the medical field, such as for catheterbased intervention therapies and remote assembly or use of micromechanical systems. There has been particular interest in the development of microactuators capable of operating in small (250–500 $\mu$m) diameter applications, such as in veins in the human brain, which enables catheter-based devices to reach and treat an aneurysm in the brain.

A recent approach to satisfying this need involves microactuators or microgrippers fabricated using known silicon-based techniques or precision micromachining, or a combination of these techniques, with the microgrippers being actuated, for example, by balloons or by shape-memory alloy (SMA) films or wires deposited on or connected to the jaws of the microgrippers. Such an approach is described and claimed in copending U.S. application Ser. No. 08/446,146, filed May 22, 1995, entitled "Microfabricated Therapeutic Actuator Mechanism", now U.S. Pat. No. 5,645,564 issued Jul. 8, 1997, assigned to the same assignee. Another recent approach involves a miniature plastic gripper constructed of either heat-shrinkable or heat-expandable plastic tubing having a cut in one end section to form gripping surfaces or jaws which are moved by inflation or deflation of an associated microballoon. Such an approach is described and claimed copending U.S. application Ser. No. 08/549,497, filed Oct. 27, 1995, entitled "Miniature Plastic Gripper And Fabrication Method", now U.S. Pat. No. 5,609,608 issued Mar. 11, 1997, assigned to the same assignee. Also, microdevices for positioning, steering, and/or sensor applications have been developed which utilize blood flow for positioning and steering of catheter-based therapeutic applications. Such microrudders, microactuators or microcantilevers are described and claimed in copending U.S. application Ser. No. 08/533,426, filed Sep. 25, 1995, entitled "Micromachined Actuators/Sensors For Intratubular Positioning/Steering", assigned to the same assignee. In addition, recent efforts have been directed to the fabrication of micromolds for the production of microballoons used, for example, angioplasty to perform interventional catheter-based minimal-invasive surgeries, wherein microballoons or microneedles having, for example, a 275 $\mu$m length and 150 $\mu$m diameter can be readily manufactured. Such a micromold is described and claimed in copending U.S. application Ser. No. 08/533,425, filed Sep. 25, 1995, entitled "Polymer Micromold And Fabrication Process", now U.S. Pat. No. 5,658,515 issued Aug. 19, 1997.

Patients with potentially life-threatening hemmorhagic brain aneurysms are in need of a safe, reliable, and fast release mechanism for the deposition of embolic platinum coils via catheters. The commercial product of current use is the Guglielmi Detachable Coil (GDC). The GDC utilizes the electrolytical dissolution of a designated guidewire junction to generate the release action. This procedure typically takes 10–30 minutes and is difficult to control in a reliable fashion. The effects of the dissolved material into the blood stream is also a potential hazard to the patient. Thus, even with the numerous prior efforts to development miniature actuators for catheter-based therapeutic application, there remains a need for safe, fast release actuator mechanisms for the delivery of embolic coils, for example.

The present invention satisfies this need, and is based on shape memory polymer (SMP), and polyurethane-based material that undergoes a phase transformation at a manufactured temperature (Tg) of choice. After the material is polymerized (cross-linked), the material is molded into its memory shape. At temperatures above Tg, the material can be easily reshaped into another configuration, and upon cooling below Tg the new shape is fixed, but upon increasing the temperature to above Tg, the material will return to its original memory shape. By inserting a GDC, for example, into an end of a SMP microtube, and applying pressures to the outside of the microtube while at a temperature above the Tg and then lowering the temperature below the Tg, the GDC is secured and retained in the microtube. After inserting the microtube and retained GDC via a catheter to a desired location, the SMP microtube is locally heated to above Tg and it returns to its original shape releasing the GDC, after which the microtube is withdrawn leaving the GDC in place.

SUMMARY OF THE INVENTION

It is an object of the present invention to provide a microfabricated therapeutic actuator.

A further object of the invention is to provide a release actuator mechanism using shape memory polymer materials.

A further object of the invention is to utilize shape memory polymer microtubing as a release actuator for the delivery of material to a point of use.

Another object of the invention is to provide a release actuator mechanism which utilizes shape memory polymer microtubing for use in catheter-based intratubular delivery of material (e.g. embolic coils) to a point of need.

Another object of the invention is to provide microfabricated therapeutic actuators constructed of shape memory polymer microtubing, wherein the shape memory is determined by a desired temperature of the application for the microtubing.

Another object of the invention is to provide a release actuator utilizing a shape memory polymer and which can be designed for remote medical applications, safety latches, connectors, and other remote applications wherein a relatively fast release time is desired.

Other objects and advantages of the present invention will become apparent from the following description and accompanying drawings. Basically, the invention involves microfabricated therapeutic actuators. More specifically, the invention involves using shape memory polymer (SMP) microtubing as a release actuator mechanism, for example, as a means for the delivery of embolic coils through catheters into aneurysms. The release actuator mechanism, aside from its medical applications can be utilized for safety latches, connectors, product delivery, etc. The SMP microtubing particularly provides a safe, reliable, and fast release mechanism for deposition of embolic platinum coils via catheters for patients with potentially life-threatening hemmorhagic brain aneurysms, wherein the speed of release is in seconds compared to the 10–30 minutes required for deposition of a conventionally used Guglielmi Detachable Coil (GDC). Further, the SMP microtubing release mechanism provides no potential hazard to the patient, such as that resulting from the electrolytical dissolution of the guidewire junction currently used to release the GDC. The SMP material, a polyurethane-based material that undergoes a phase transformation at a manufactured temperature (Tg). The SMP material can be constructed so as to be inert to any fluids of the human body, for example, and can be constructed to be responsive to various desired phase transformation temperatures, Tg, above which the material is soft and reshapable and then by cooling the material below the Tg, the material retains the reshaped configuration until it is again heated to above the Tg temperature at which time the SMP material returns to its original memory shape. Thus, by heating the SMP material, inserting therein an embolic platinum coil, or other device, applying pressure to the SMP material about the inserted coil while subsequent by cooling, the coil is retained until released by again heating the SMP material to the temperature at which the material returns to its original shape. Thus, a coil retained in an SMP microtube can be readily inserted via a catheter to a point of use, such as a brain aneurysm. The SMP microtubing can be manufactured, for example, to pass through passageways, such as blood vessels having inner diameters in the range of 250–1000 microns.

BRIEF DESCRIPTION OF THE DRAWINGS

The accompanying drawings, which are incorporated into and form a part of the disclosure, illustrate embodiments of the invention and an embodiment of a procedure for carrying out the invention and, together with the description, serve to explain the principles of the invention.

DETAILED DESCRIPTION OF THE INVENTION

Figure 1A:
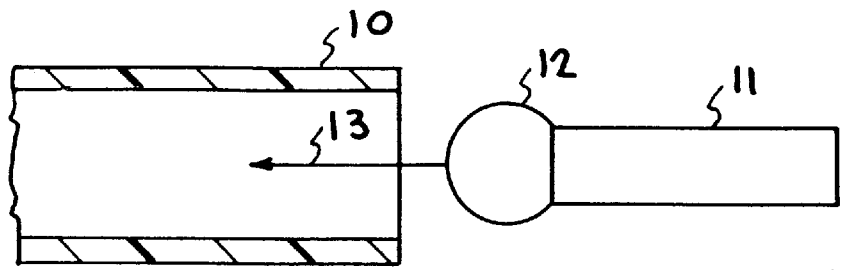
FIGS. 1A to 1E schematically illustrate the loading and release sequence for an object in a shape memory polymer (SMP) microtubular release mechanism.

The present invention is directed to microfabricated therapeutic actuators using shaped memory polymer (SMP) microtubing. These miniature actuators are of particular interest for use within a small diameter passageways, such as blood vessels having diameters of about 250–1000 microns. The SMP microtubing may function, for example, as a release actuator mechanism for the delivery of embolic coils through catheters into aneurysms. These microfabricated actuators may also find use as a release mechanism for safety latches, connectors, and various other medical applications. Shaped memory polymers manufactured by Memory Corporation, can be formed into various configurations and sizes, and thus can be manufactured as small diameter microtubing capable of operating in a 250–1000 micron diameter blood vessel or other passageway. SMP is a polyurethane-based material that undergoes a phase transformation at a manufactured temperature, Tg. After the material is polymerized (cross-linked), the material is molded into its memory shape. At a temperature above the Tg, the material is soft and can easily be arbitrarily reshaped by applying pressure into another configuration. The elastic constant of the material can change by about 200 times when undergoing this phase transformation. As the temperature is lowered, with the pressure applied, to a temperature below the Tg, this new shape is fixed and locked in as long as the material stays below the Tg. However, if the temperature reheats to above the Tg, the material will return to its original memory shape. The SMP material can be heated thermally, resistively, optically, by heated fluid.

By inserting into an SMP microtubing, having a specified manufacture temperature, Tg, an end of an embolic platinum coil, for example, heating the microtubing to a temperature above the Tg, applying pressure to the microtubing causing it to conform to the configuration of the end of the coil, and then cooling to a temperature below the Tg, the end of the coil is retained or loaded in the SMP microtubing. The SMP microtubing is then attached to the end of a guide wire or other guidance means and the platinum coil is loaded outside the body of a patient. The guide wire and the loaded coil are then pushed through a catheter in a blood vessel of the body, and at a desired point of use, a brain aneurysm or affected area, for example, the SMP microtubing is heated to a temperature above the Tg thereof, such as by injecting warm water through the catheter, whereby the SMP microtubing returns to its original memory shape and the end of the coil is released at the desired point of use, whereafter the guide wire and attached SMP microtubing is removed via the catheter. The microtubing can be then cleaned for reuse or disposed of.

The microfabricated SMP actuator or release mechanism of this invention can improve the speed of release of the coil to seconds, compared to the previous 10–30 minutes using the currently used Guglielmi Detachable Coil described above, and is much more reliable with no known safety hazards to the patient. The release mechanism can also be used in other medical applications requiring the controlled deposition of therapeutic materials, as well as in various non-medical applications. Such as the SMP tubing can be manufactured in various sizes and with different Tg temperatures, its use as a release mechanism greatly expands the field of micro-devices for numerous applications.

Figure 1B:
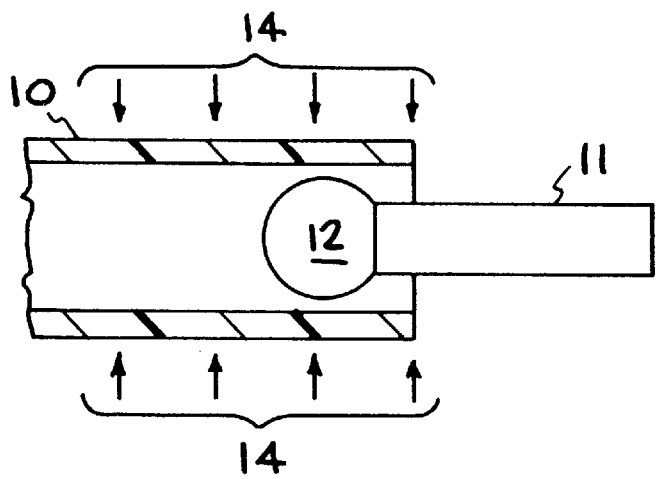
Figure 1C:
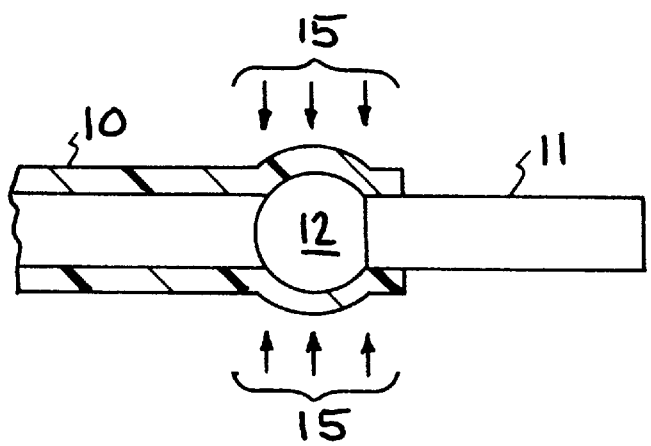
Figure 1D:
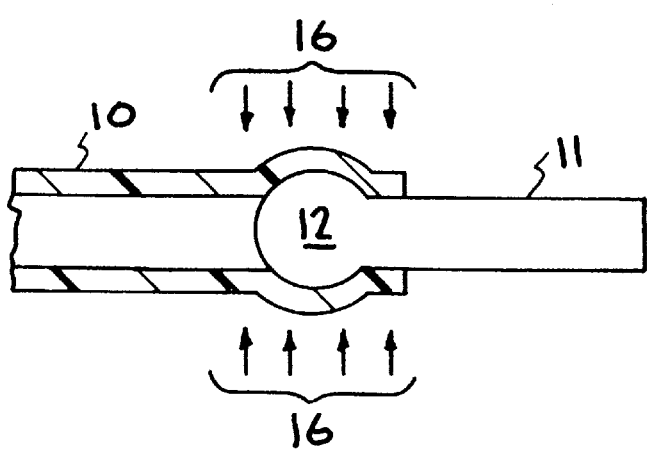
Figure 1E:
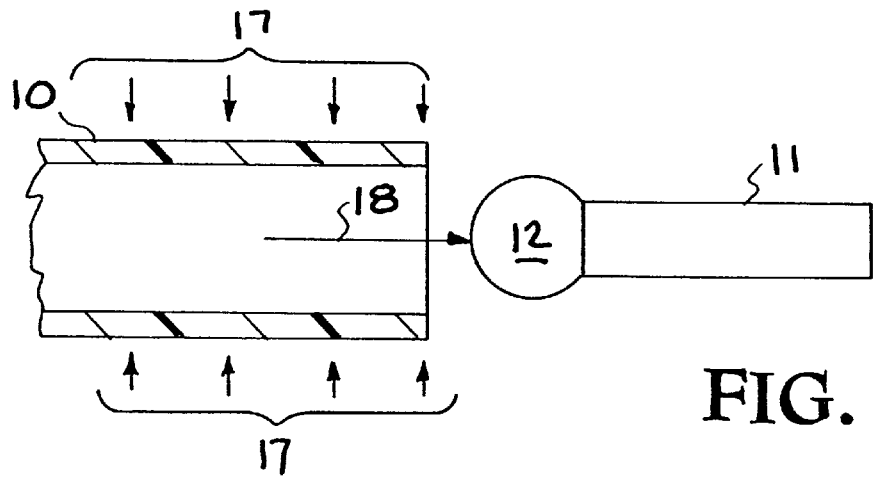

The following description, with reference to FIGS. 1A–1E, sets forth an example of the invention, and loading/release sequence, for use as a release mechanism for therapeutic material, such as an embolic platinum coil. A shape memory polymer (SMP) is manufactured to dimension and shape for an intended target or use, and with a specific phase transformation temperature, Tg. FIGS. 1A–1E illustrate the loading and release procedure of a straight SMP hollow member or tubing grabbing onto a coil with a ball end. In FIG. 1A the tubing or hollow member 10 is in its original size and shape and a coil 11 having a ball-end 12 can be loaded into the tubing 10 as indicated by arrow 13. The tubing 10 is heated above the Tg to soften the SMP material, as indicated at 14 in FIG. 1B, and then pressure is applied to the tubing 10 in the area of the ball-end 12, as indicated at 15 in FIG. 1C, whereby the tubing 10 is press-fitted over the ball-end 12 of coil 11. The joined ends of tubing 10 and coil 11 are then subjected to cooling to temperature below Tg, as indicated at 16 in FIG. 1D, which stiffens or hardens the SMP material and creates a solid hold of the ball-end 12 of coil 11 by the end of the SMP tubing 10. To release the coil 11 from SMP tubing, the joined area of the tubing 10 is simply reheated as indicated at 17 to above the Tg, the tubing 10 expands to its original opening and the coil 11 is released as indicated by arrow 18, as shown in FIG. 1E. The reheating of tubing 10 as indicated in FIG. 1E can be carried out by injecting warm water, for example, through the tubing. The tubing 10 can also be heated and/or reheated by resistive heating, optical heating, or thermal heating.

The amount of heating, pressure, cooling, and reheating is dependent of the diameter and Tg of the SMP tubing. For example, with an SMP tubing 10 having an internal diameter of 250 μm, an external diameter of 350 μm, and Tg of 45° C., with the coil 11 having a diameter of 200 μm with a ball-end 12 diameter of 250 μm, the SMP tubing is initially heated to a temperature of 48° C., and a pressure of 10 psi is applied to the tubing while maintaining the heat on the tubing to form the press-fit of the tubing around the ball-end of the coil. The SMP tubing is thereafter cooled to a temperature of 37° C., while maintaining the applied pressure, whereby the ball-end of the coil is fixedly retained in the SMP tubing. The coil is released from the SMP tubing by injecting water at a temperature of 48° C. through the tubing which causes the tubing temperature to raise above the Tg thereof. The SMP tubing can be fabricated with internal diameter of 100 μm to 1000 μm, an external diameter of 150 μm to 1 mm, and with a Tg in the range of −30° C. to 100° C.

Figure 2:
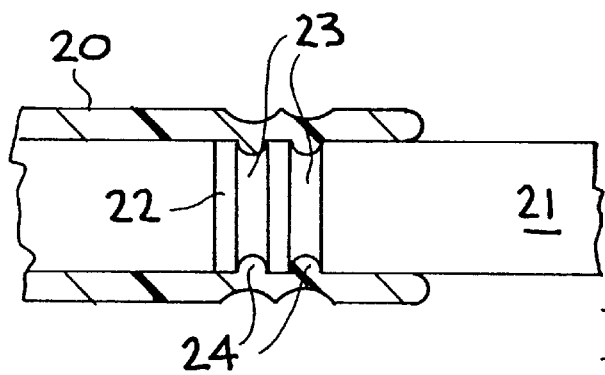
FIGS. 2 and 3 illustrate another embodiment where the end of the inserted object (embolic coil) has a grooved end for better gripping.
Figure 3:
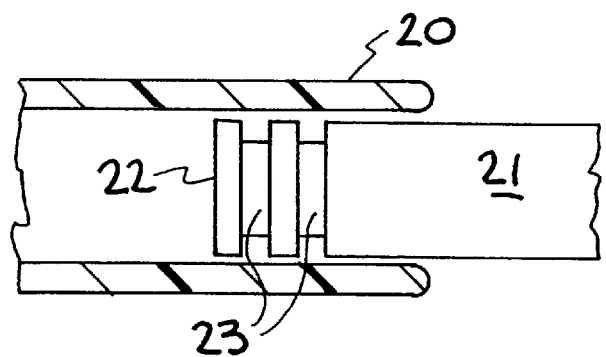

The embodiments of FIGS. 2 and 3 differ from the FIGS. 1A–1E embodiment by replacing the ball at the coil end with a treaded or grooved end, with release being accomplished by directing heated fluid through the microtubing, as described above, or by an external wave field, such as magnetic or RF, to induce resistive heating. As shown in FIGS. 2, an SMP tubing 20 is processed as described above in FIGS. 1A–1D to retain therein an object 21, such as an embolic coil, having an end 22 which is provided with a plurality of grooves 23. After insertion of the end 22 of object 21 and initial heating of SMP tubing 20, as shown in FIGS. 1A–1B, and applying pressure about the grooves 23 of end 22 and cooling of the SMP tubing 20, as shown in FIGS. 1C–1D, the material of SMP tubing extends into the grooves 23, as indicated at 24, which provides a more secure grip or retention of the end 22 of object 21 (embolic coil) than the ball-end 12 of coil 11 in FIGS. 1A–1E, due to the grooved arrangement of end 22. As shown in FIG. 3, upon heat the SMP tubing 20 above the temperature Tg, the tubing 20 returns to its original shape, thereby releasing the end 22 of object 21. Heating of the SMP tubing 20 can be accomplished via induced resistive heating of the end 22 of object 21 by an external wave field, such as by an associated magnetic or radio frequency (RF) source, provided of cause that the end 22 of object 21 is constructed of material inductive of resistance heating. External heating of the end 22 of object 21 can be carried out through electrical induction or electrothermal heating (through a dielectric lossy material on the end of the coil). An example is by applying an external alternating magnetic field to Ni-Pd material coated on at least the end 22 of object or coil 21.

Figure 4:
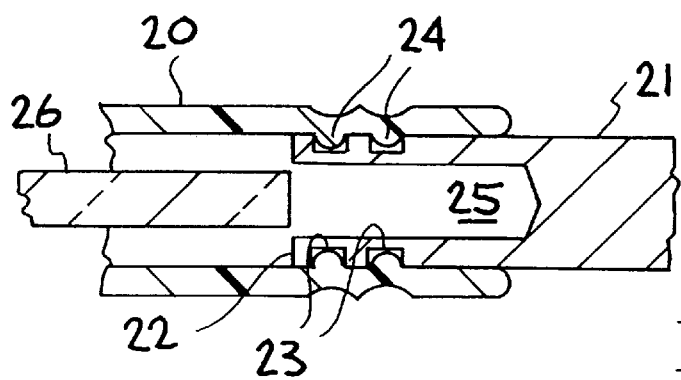
FIG. 4 illustrates an embodiment similar to FIG. 2 with a light trap release arrangement.

The FIG. 4 embodiment is similar to the FIG. 2 embodiment, except for means by which the SMP tubing can be reheated optically to release the end 22 of object or coil 21. Optical heating provides a more uniform and core efficient method to heat the coil. This is accomplished by providing the end 22 of object 21 with a light trap or cavity 25, which functions to heat the SMP tubing 20 by directing light in the trap 25 by an optical fiber 26, which extends through an associated catheter into SMP tubing 20. Upon optically heating the SMP tubing to its temperature Tg, the tubing 20 returns or reverts to its original shape, as shown in FIG. 3, releasing the end 22 of object 21.

It has thus been shown that the present invention provides microfabricated actuators using SMP microtubing as a release mechanism for the delivery of an item, such as therapeutic materials, and which can operate in areas having a diameter as small as 250–1000 microns. While the invention has particular application in the medical field, such as delivery of embolic coils through catheters to aneurysms, it can be utilized for controlled deposition of items in non-medical fields.

While a particular embodiment and operational sequence has been illustrated and described, along with materials, parameters, etc., to exemplify and teach the principles of the invention, such are not intended to be limiting. Modifications and changes may become apparent to those skilled in the art, and it is intended that the invention be limited only by the scope of the appended claims.

The invention claimed is:

1. A method for providing controlled deposition of an object, comprising:
    providing a quantity of shape memory polymer material;
    positioning at least a portion of an object to be deposited into at least a portion of the shape memory polymer material;
    heating the material to a temperature above a temperature Tg causing softening of the material;
    applying pressure to the heated material causing the material to reshape about the object positioned therein; and
    cooling the material to a temperature below Tg causing the material to harden and retain the object therein.

2. The method of claim 1, additionally including positioning the object at a point of use, releasing the object from the material by heating the material to above the temperature Tg, and removing the material.

3. The method of claim 2, wherein heating the material to above the temperature Tg is carried out by one of the group consisting of fluid heating, thermal heating, resistive heating, and optical heating.

4. The method of claim 2, wherein the object to be deposited is a therapeutic material, wherein the positioning of the object is carried out using a catheter, and wherein the heating of the material is carried out using a heated fluid injected through the catheter, thermal heating, resistive heating, or optical heating.

5. A method for retaining and releasing an object from a quantity of shape memory polymer material comprising:
    positioning at least a portion of an object to be retained and released into at least a portion of the shape memory polymer material;
    heating the shape memory polymer material to a temperature above a temperature Tg causing softening of the material;
    applying pressure to the softened material causing the material to reshape about at least a portion of the object positioned therein;
    cooling the material to a temperature below the temperature Tg causing the material to harden and retain the object therein; and
    reheating the material to a temperature above the temperature Tg causing the material to soften and return to its original configuration thereby enabling the object retained therein to be released therefrom.

6. The method of claim 5, wherein cooling of the material is carried out while pressure is being applied to the material.

7. The method of claim 5, additionally including positioning the retained object at a point of use prior to reheating the material whereby the object is released at the point of use.

8. The method of claim 7, wherein the object comprises a therapeutic material, wherein positioning the object at a point of use is carried out by a catheter, and wherein the heating and reheating of the material is carried out using a heated fluid which can be injected through the catheter, thermal heating, resistive heating, and optical heating.

9. The method of claim 5, wherein heating and reheating of the material is carried out by at least one of the group consisting of fluid heating, thermal heating, resistive heating, and optical heating.

* * * * *